United States Patent
Hirayama et al.

(10) Patent No.: US 10,806,418 B2
(45) Date of Patent: Oct. 20, 2020

(54) X-RAY CT APPARATUS AND IMAGING CONDITION CALCULATING METHOD

(71) Applicant: CANON MEDICAL SYSTEMS CORPORATION, Otawara-shi (JP)

(72) Inventors: Hiroshi Hirayama, Koto (JP); Sanae Harada, Nasushiobara (JP); Toyomasa Honda, Nasushiobara (JP)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 180 days.

(21) Appl. No.: 15/994,178

(22) Filed: May 31, 2018

(65) Prior Publication Data

US 2018/0344275 A1 Dec. 6, 2018

(30) Foreign Application Priority Data

May 31, 2017 (JP) .................. 2017-107336
May 30, 2018 (JP) .................. 2018-103546

(51) Int. Cl.
- A61B 6/00 (2006.01)
- A61B 6/03 (2006.01)
- A61B 6/02 (2006.01)
- A61B 6/04 (2006.01)

(52) U.S. Cl.
CPC .............. *A61B 6/463* (2013.01); *A61B 6/027* (2013.01); *A61B 6/032* (2013.01); *A61B 6/0457* (2013.01); *A61B 6/4035* (2013.01); *A61B 6/488* (2013.01); *A61B 6/542* (2013.01); *A61B 6/464* (2013.01)

(58) Field of Classification Search
CPC ......... A61B 6/463; A61B 6/027; A61B 6/032; A61B 6/0457; A61B 6/4035; A61B 6/488; A61B 6/542; A61B 6/464
USPC ....................................................... 378/4–20
See application file for complete search history.

(56) References Cited

U.S. PATENT DOCUMENTS

2004/0086076 A1 5/2004 Nagaoka et al.
2006/0013358 A1* 1/2006 Seto .................. A61B 6/032
378/16

FOREIGN PATENT DOCUMENTS

JP 2002-263097 9/2002
JP 2007-7255 1/2007

* cited by examiner

*Primary Examiner* — Courtney D Thomas
(74) *Attorney, Agent, or Firm* — Oblon, McClelland, Maier & Neustadt, L.L.P.

(57) ABSTRACT

According to one embodiment, an X-ray CT apparatus includes processing circuitry. The processing circuitry acquires a plurality of discrete images at a corresponding plurality of discrete positions in a body axis direction of an object, and calculates imaging conditions corresponding to a scan range of a main scan based on the plurality of discrete images.

17 Claims, 9 Drawing Sheets

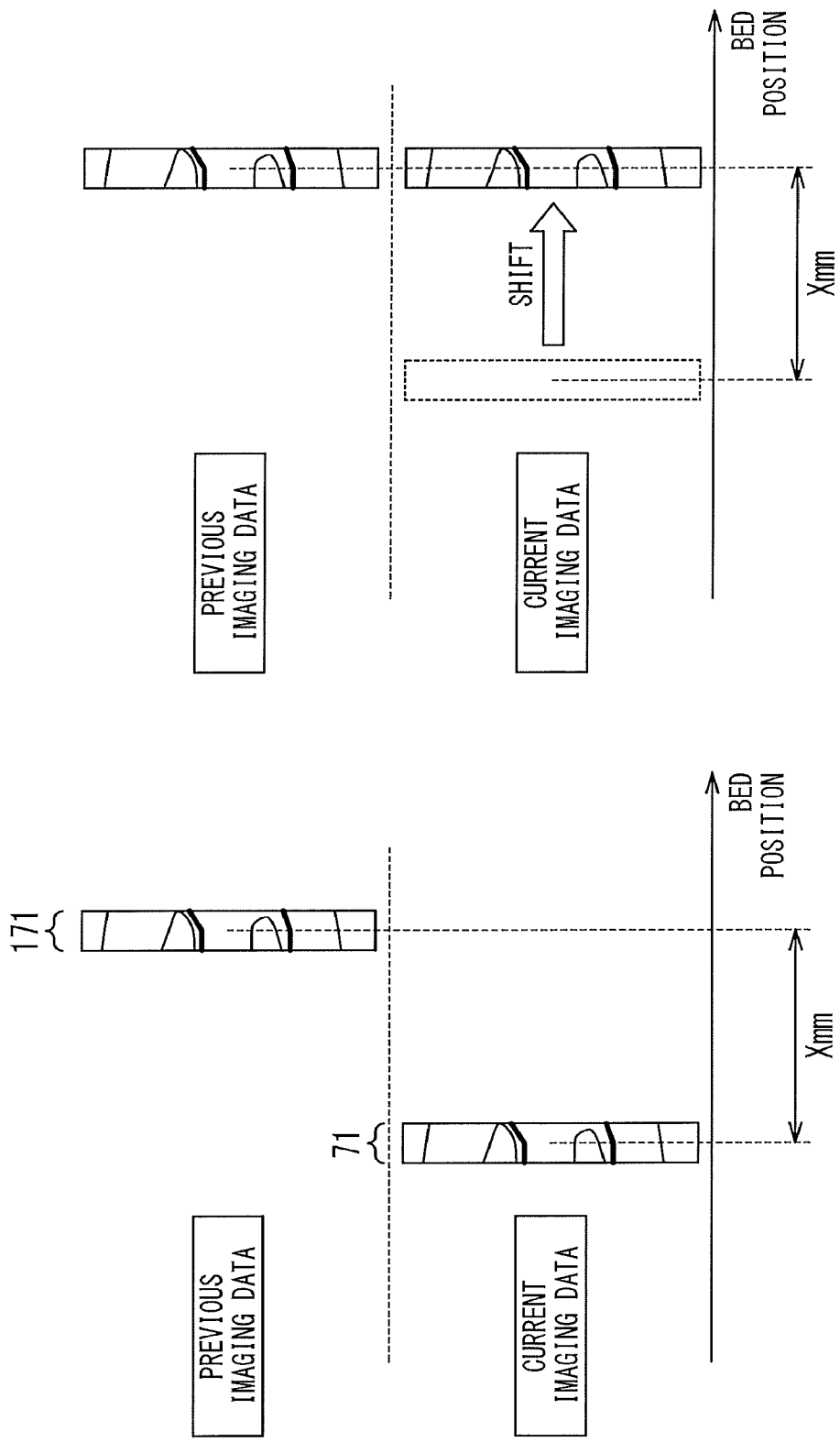

X-RAY CT APPARATUS AND IMAGING CONDITION CALCULATING METHOD

CROSS-REFERENCE TO RELATED APPLICATIONS

This application claims the benefit of priority of Japanese Patent Application No. 2017-107336, filed May 31, 2017, and Japanese Patent Application No. 2018-103546, filed May 30, 2018, the entire contents of all of which are incorporated herein by reference.

FIELD

Embodiments described herein relate generally to an X-ray CT apparatus and an imaging condition calculating method.

BACKGROUND

When imaging an object with an X-ray CT (Computed Tomography) apparatus, a scanography (scout imaging, an imaging for obtaining scanogram) may be performed before the main scan to obtain a scanogram. By using the scanogram, it is possible to accurately perform positioning for the main scan (setting of a range for obtaining tomographic image, hereinafter referred to as a scan range) and setting of imaging conditions for the main scan.

However, the scanography, which is performed before the main scan for the positioning for the main scan and the setting of the imaging conditions, is often performed by irradiating X-rays continuously in time. In this case, the exposure dose of the object increases because, though the tube current used in the scanography is lower than that in the main scan, the scanogram tends to take a long time.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4A is an explanatory diagram showing an example of a state in which the criterial image of the reference image and the criterial image imaged before the main scan are collated;

FIG. 4B is an explanatory diagram showing an example of a state in which the criterial image of the reference image and the criterial image imaged before the main scan are aligned on the image;

DETAILED DESCRIPTION

Hereinbelow, a description will be given of an X-ray CT apparatus and an imaging condition calculating method according to embodiments of the present invention with reference to the drawings.

In general, according to one embodiment, an X-ray CT apparatus includes processing circuitry. The processing circuitry acquires a plurality of discrete images at a corresponding plurality of discrete positions in a body axis direction of an object, and calculates imaging conditions corresponding to a scan range of a main scan based on the plurality of discrete images.

Figure 1:
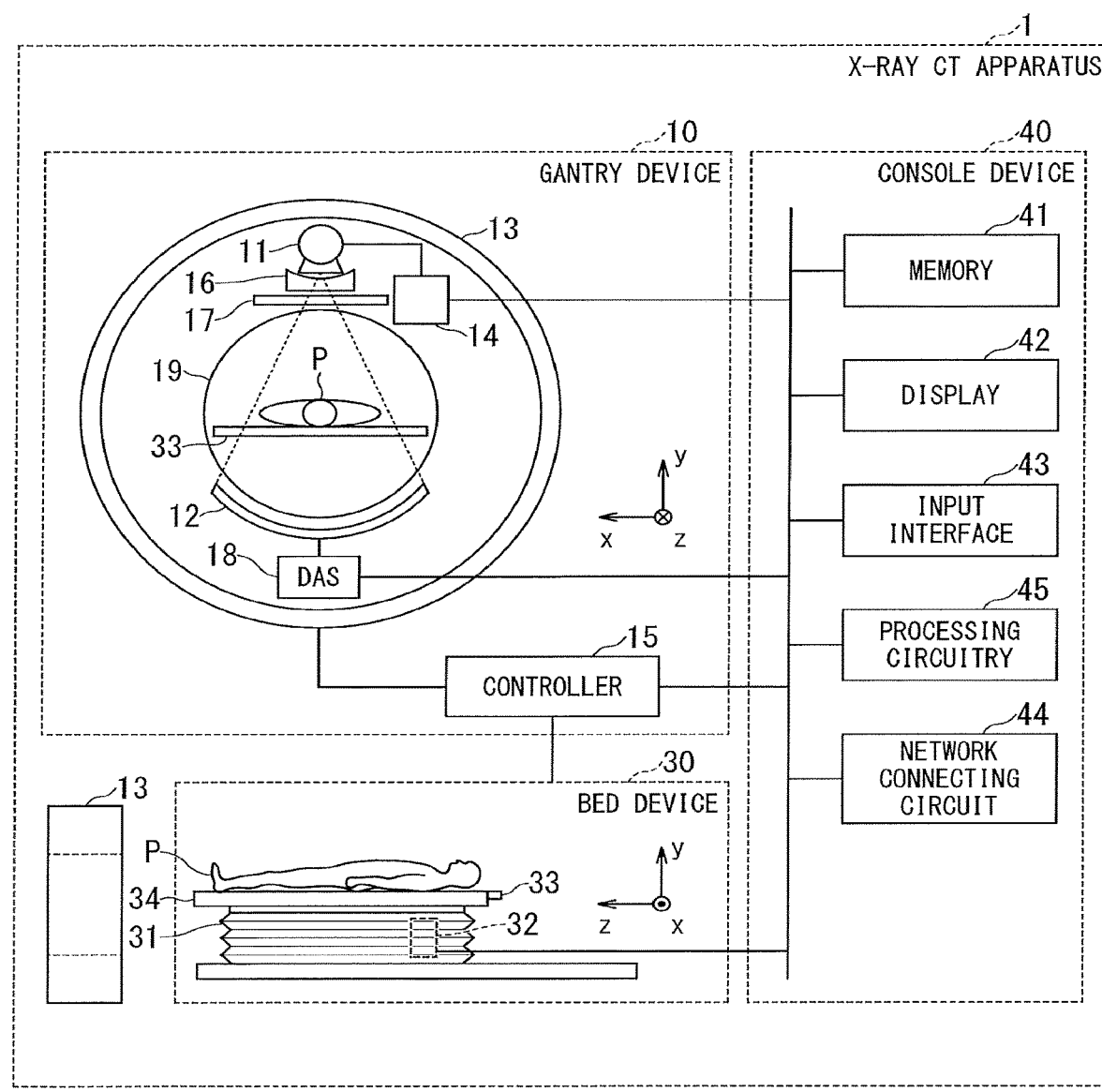
FIG. 1 is a block diagram to show an example of an X-ray CT apparatus according to the present embodiment.

FIG. 1 is a block diagram to show an example of an X-ray CT apparatus 1 according to the present embodiment. In the present embodiment, the rotational axis of the rotating frame 13 in the non-tilted state or the longitudinal direction of the tabletop 33 of the bed device 30 is defined as the z-axis direction, the direction orthogonal to the z-axis and parallel to the floor surface is defined as the x-axis direction, and an axial direction perpendicular to the floor surface is defined as the y-axis direction (see FIG. 1).

The X-ray CT apparatus 1 includes a gantry device 10, a bed device 30, and a console device 40.

The X-ray CT apparatus and the imaging condition calculation method according to the present embodiment are applicable to an imaging with tube current modulation (hereinafter referred to as tube current modulation imaging) or an imaging with tube voltage modulation (hereinafter referred to as tube voltage modulation imaging), and can perform the scanography to obtain the scanogram before the main scan.

The X-ray CT apparatus 1 may be configured as any one of different types, such as a so-called third generation CT apparatus, i.e., an Rotate/Rotate type in which an X-ray tube and an X-ray detector integrally rotate about an object, or as a so-called fourth generation CT apparatus, i.e., an Stationary/Rotate type or an Nutate/Rotate type in which multiple detecting elements are circularly arrayed and only the X-ray tube rotates about the object. In the following, an example of adopting the third generation Rotate/Rotate type as the X-ray CT apparatus 1 according to the present embodiment is explained.

The gantry device 10 includes an X-ray tube 11, an X-ray detector 12, a rotating frame 13 having an opening portion 19 in which an imaging region resides, an X-ray high voltage device 14, a controller 15, a wedge 16, a collimator 17, and a DAS (Data Acquisition System) 18.

The X-ray tube 11 is a vacuum tube that irradiates thermoelectrons from a cathode (filament) to an anode (target) by applied a high voltage from the X-ray high voltage device 14.

The X-ray tube according to this embodiment is applicable to a single tube type X-ray CT apparatus, and also applicable to a so-called multi-tube type X-ray CT apparatus in which a plurality of pairs of an X-ray tube and an X-ray detector is mounted on a rotating ring. Further, the hardware for generating the X-rays is not limited to the X-ray tube 11. For example, instead of the X-ray tube 11, the X-ray generator of the fifth generation type can be used which includes a focus coil for focusing the electron beam generated from the electron gun, a deflection coil for electromagnetically deflecting the electron beam, and the target ring enclosing a half circumference of the object P and generating the X-rays by collided with the deflected electron beam.

The X-ray detector 12 detects X-rays that is irradiated from the X-ray tube 11 and passes through the object P, and outputs an electric signal corresponding to the detected amount of X-rays to the DAS 18. The X-ray detector 12 has, for example, a plurality of X-ray detection element arrays in which a plurality of X-ray detection elements are arrayed in the channel direction along one circular arc around the focus of the X-ray tube 11. For example, the X-ray detector 12 has a structure in which the plurality of X-ray detection element arrays in the channel direction is arrayed in a slice direction (column direction, row direction).

The X-ray detector 12 is, for example, an indirect conversion type detector having a grid, a scintillator array, and an optical sensor array. The scintillator array has a plurality of scintillators, and each scintillator has a scintillator crystal that outputs light with an amount of photons corresponding to the amount of incident X-rays. The grid is disposed on the X-ray incident side of the scintillator array and has an X-ray shielding plate having a function of absorbing scattered X-rays. The optical sensor array has a function of converting the light from the scintillator into an electric signal corresponding to the amount of the light from the scintillator, and has, for example, an optical sensor such as a photomultiplier tube (PMT).

The X-ray detector 12 may be a direct conversion type detector having a semiconductor element for converting incident X-rays into electric signals.

The rotating frame 13 is an annular frame that supports the X-ray tube 11 and the X-ray detector 12 so as to face each other and rotates the X-ray tube 11 and the X-ray detector 12 by the controller 15 described below. In addition to the X-ray tube 11 and the X-ray detector 12, the rotary frame 13 further includes and supports the X-ray high voltage device 14 and the DAS 18. The detection data generated by the DAS 18 is transmitted from a transmitter having a light emitting diode (LED) provided in the rotating frame 13 by optical communication to a receiver having a photo diode provided in a non-rotating portion of the gantry device 10, e.g., a fixed frame (not shown), and is then transferred to the console device 40. The method of transmitting the detection data from the rotating frame 13 to the non-rotating part of the gantry device 10 is not limited to the above-mentioned optical communication, and any method may be adopted as long as it is non-contact type data transmission. A fixed frame (not shown) is a frame that rotatably supports the rotating frame 13.

The X-ray high voltage device 14 has electric circuits such as a transformer and a rectifier, and has a high voltage generating device generating a high voltage to be applied to the X-ray tube 11, and an X-ray control device that controls an output voltage of the high voltage generating device according to X-rays irradiating from the X-ray tube 11. The high voltage generating device may be a transformer type or an inverter type. The X-ray high voltage device 14 may be provided on the rotating frame 13 or on the fixed frame side of the gantry device 10.

The controller 15 has a processor and a memory, and a driving mechanism such as a motor and an actuator. The controller 15 receives an input signal from an input interface attached to the console device 40 or the gantry device 10, and controls the gantry device 10 and the bed device 30. For example, the controller 15 performs rotation control of the rotating frame 13 in response to the input signal, tilt control of the gantry device 10, and driving control of the bed device 30 and the tabletop 33. The tilt control of the gantry device 10 is made by the controller rotating the rotating frame 13 around an axis parallel to the X axis direction on the basis of the tilt angle information input by the input interface attached to the gantry device 10. The controller 15 may be provided in the gantry device 10 or may be provided in the console device 40.

The wedge 16 is a filter for adjusting the amount of X-rays irradiated from the X-ray tube 11. Specifically, the wedge 16 transmits and attenuates the X-rays irradiated from the X-ray tube 11 such that the X-rays applied to the object P from the X-ray tube 11 have a predetermined distribution. For example, the wedge 16 (wedge filter, bow-tie filter) is a filter in which aluminum is processed to have a predetermined target angle or a predetermined thickness.

The collimator 17 is a lead plate or the like for narrowing the irradiation range of the X-rays transmitted through the wedge 16, and forms a slit by combining a plurality of lead plates or the like.

The DAS 18 includes an amplifier that performs amplification processing on electric signals output from the respective X-ray detecting elements of the X-ray detector 12 and an A/D converter that converts the electric signals into digital signals, and generates detection data. The detection data generated by the DAS 18 is transferred to the console device 40.

The bed device 30 is a device for placing and moving the object P to be scanned, and includes a base 31, a bed driving device 32, the tabletop 33, and a support frame 34.

The base 31 is a casing that supports the support frame 34 movably in the vertical direction (y direction). The bed driving device 32 is a motor or an actuator that moves the tabletop 33 on which the object P is placed in the longitudinal direction (z direction) of the tabletop 33. A tabletop 33 provided on the upper surface of the support frame 34 is a plate on which the object P is placed.

In addition to the tabletop 33, the bed driving device 32 may move the support frame 34 in the long axis direction (z direction) of the tabletop 33. Further, the bed driving device 32 may be moved together with the base 31 of the bed device 30. In the case where the present invention can be applied to a standing CT (an X-ray CT apparatus adapted to a standing object), the patient movement mechanism may be moved instead of the tabletop 33. Further, in the case of imaging involving a relative change in the positional relationship between the imaging system of the gantry device 10 and the tabletop 33, such as a helical scan and the scanography for the setting of the range (scan range) for obtaining tomographic images in the main scan (hereinafter referred to as "the scanography for the positioning for the main scan"), the relative change of the positional relationship may be performed by driving the tabletop 33, or the gantry device 10, or by a combination thereof.

The console device 40 has a memory 41, a display 42, an input interface 43, a network connecting circuit 44, and a processing circuitry 45. It is noted that the console apparatus 40 will be described as executing all functions with a single console in the present embodiment, but these functions may be executed by a plurality of consoles.

The memory 41 includes a processor-readable recording medium such as a semiconductor memory element, e.g., a RAM (Random Access Memory) or a flash memory, a hard disk, an optical disk, and the like. The memory 41 stores, for example, projection data and reconstructed image data. The projection data and the reconstructed image data generated by the X-ray CT apparatus 1 may be stored in the memory 41, or may be stored in another electronic device such as a cloud server connectable to the X-ray CT apparatus 1 via the network upon receiving a storage request from the X-ray CT apparatus 1. A part or all of the programs and data in the recording medium of the memory 41 may be downloaded by communication via a network, or may be given to the memory 41 via a portable storage medium such as an optical disc.

In addition, it is preferable that the memory 41 stores in advance a past image which was obtained by imaging the object P in the past with a modality or an optical camera. The past image may be acquired from the image server or the like via the network by the processing circuitry 45 and stored in the memory 41.

The past image is one of the reference image used in performing positioning for the main scan (setting of the scan range) to be described later. The reference image according to the present embodiment includes at least an image of a predetermined criterial position of the object P (hereinafter referred to as a criterial image) used in the positioning for the main scan. As the modality to obtain the past image other than the X-ray CT apparatus 1, the various modalities can be used such as a magnetic resonance imaging (MRI) apparatus, an ultrasonic diagnostic apparatus, or the like. For example, if the modality for obtaining a past image is the X-ray CT apparatus 1 itself, the previous image may be the scanogram generated by the scanography.

The display 42 displays various kinds of information. For example, the display 42 outputs a medical image (CT image) generated by the processing circuitry 45, a GUI (Graphical User Interface) for receiving various operations from the user, and the like. For example, the display 42 is a liquid crystal display, CRT (Cathode Ray Tube) display, OLED (Organic Light Emitting Diode) display, or the like.

The input interface 43 accepts various input operations from the user, converts the accepted input operations into electric signals, and outputs them to the processing circuitry 45. For example, the input interface 43 receives from the user the collection conditions for collecting projection data, the reconstruction conditions for reconstructing a CT image, the image processing conditions for generating a post-processing image from a CT image, and the like. For example, the input interface 43 is a mouse, a keyboard, a trackball, a switch, a button, a joystick, or the like.

The network connecting circuit 44 implements various information communication protocols according to the network. The network connecting circuit 44 connects the X-ray CT apparatus 1 and other devices such as an image server in accordance with these various protocols. For this connection, electrical connection via an electronic network or the like can be applied. The network refers to a general information communication network using telecommunications technology and includes not only a wireless/wired LAN hospital backbone local area network (LAN) and the Internet network, but also a telephone communication network, an optical fiber communication network, a cable communication network, a satellite communication network, and other networks.

The processing circuitry 45 is a processor configured to execute, by reading out and executing the program stored in the memory 41, a process for reducing the exposure dose of the object P in the scanography performed before the main scan for positioning for the main scan and for setting of imaging conditions for the main scan. The processing circuitry 45 also controls the entire operation of the X-ray CT apparatus 1.

Figure 2:
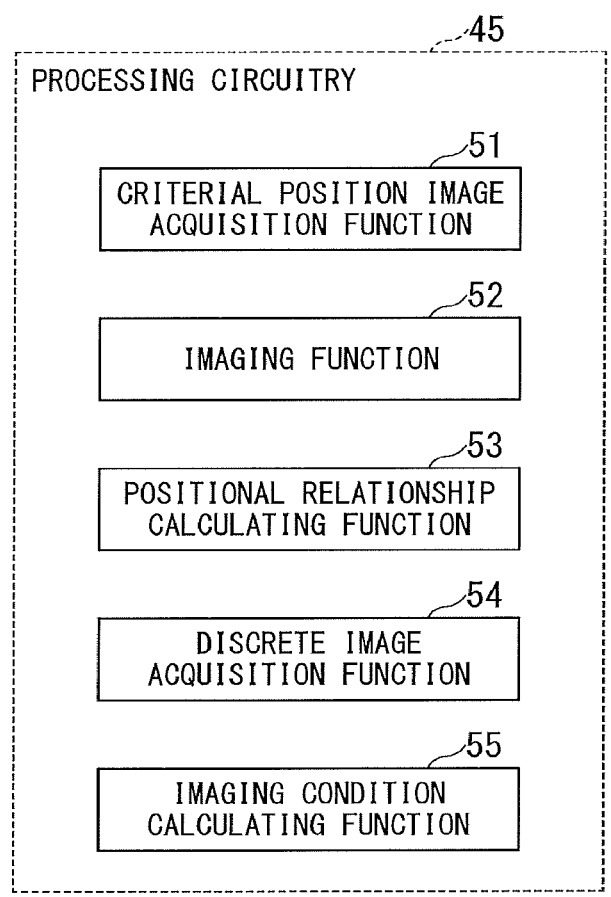
FIG. 2 is a block diagram illustrating the function of processor of the processing circuitry.

FIG. 2 is a block diagram illustrating the function of processor of the processing circuitry 45. As shown in FIG. 2, the processor of the processing circuitry 45 implements the criterial position image acquisition function 51, the imaging function 52, the positional relationship calculating function 53, the discrete image acquisition function 54, and the imaging condition calculating function 55. Each of these functions is stored in the memory 41 in the form of a program.

In the present embodiment, an example in which each function 51-55 is implemented by the processing circuitry 45 of the console device 40 will be described, but some or all of these functions 51-55 of the processing circuitry 45 may be implemented by an external device having at least a processor and a memory circuit such as a server installed in a hospital, a cloud console, a workstation or the like connected to the X-ray CT apparatus 1.

The criterial position image acquisition function 51 acquires a reference image including a predetermined criterial position of the object P when an image used in the positioning for the main scan (hereinafter, referred to as a positioning image) is required. The reference image is the image including at least the criterial image (the image of predetermined criterial position of object P) in the image. For example, even in the case of performing the main scan with tube current modulation, there is a case where accurate positioning using a scanogram is not performed in health checks or the like. In this case, it is not necessary to acquire the positioning image for the main scan.

The imaging function 52 images object P in the main scan with tube current modulation or with tube voltage modulation, or the main scan combining tube current modulation and tube voltage modulation. In addition, the imaging function 52 obtains the criterial image 71 by scanographing the predetermined criterial position of the object P before the main scan. The criterial image 71 is a scanogram having a predetermined width which a predetermined criterial position of object P is included therein, and includes the image of the predetermined criterial position of object P.

The criterial image 71 is imaged before the main scan, preferably on the same day of the main scan, more preferably just before the main scan. For example, the imaging of the criterial image 71 is preferably included in the same scan protocol as the pulse scanography described below. In this case, since the criterial image 71 is imaged during execution of the same scan protocol as that of the pulse scanography, the criterial image 71 is imaged immediately before the main scan like the plurality of discrete images obtained by the pulse scanography. In this case, it can be said that the state of the object P at the time of imaging the criterial image 71 and the plurality of discrete images is almost the same as the state at the time of performing the main scan.

Figure 3:
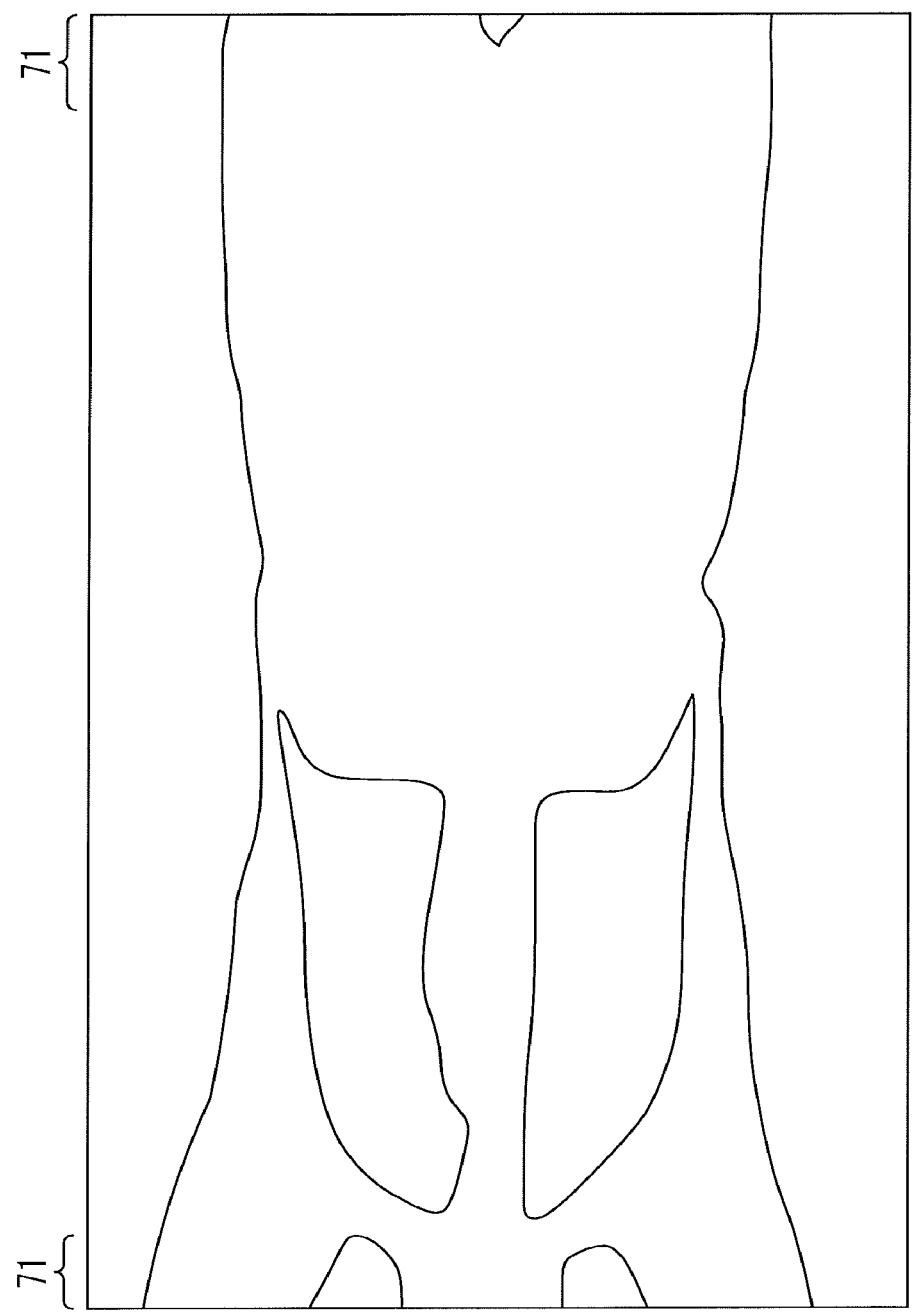
FIG. 3 is a diagram for explaining a criterial image imaged before the main scan.

FIG. 3 is a diagram for explaining the criterial image 71 imaged before the main scan. FIG. 4A is an explanatory diagram showing an example of the state in which the criterial image 171 of the reference image and the criterial image 71 imaged before the main scan are collated. FIG. 4B is an explanatory diagram showing an example of the state in which the criterial image 171 of the reference image and the criterial image 71 imaged before the main scan are aligned on the images.

The criterial image 71 imaged before the main scan is used for alignment on the images (image alignment). The predetermined criterial position to be included in the criterial image 71 imaged before the main scan is preferably a part in the human body where the absorbed dose is not easily change over time. A plurality of criterial positions may be set. For example, in the case where the past image is used as the reference image and the height of the object P is greatly different between the imaging time of the past image and the present time, it is possible to easily grasp that the height of the object P has changed by using two or more points different in the body axis direction as the criterial positions. Also, the criterial position may be the end of the scan range of the main scan, which is included in the imaging condition of the main scan, and further, both ends of the scan range may be used as the criterial positions (see FIG. 3).

When performing positioning for the main scan, the positional relationship calculating function 53 collates the criterial image 171 included in the reference image with the criterial image 71 imaged before the main scan (see FIG. 4A). Next, the positional relationship calculating function 53 aligns the criterial image 171 of the reference image and the criterial image 71 imaged before the main scan (see FIG. 4B). At this time, the difference (see Xmm in FIGS. 4A and 4B) between the criterial image 171 of the reference image and the criterial image 71 imaged before the main scan is calculated. After the image alignment, positioning (setting of the scan range) for main scan is performed using the reference image, and the scan start position is determined. In the case where the reference image is the past image taken by a modality in the past and tabletop position information is attached to the past image, the positional relationship calculating function 53 can move the object P to the start position of the main scan by adjusting the relative position of the tabletop 33 on which the object P is placed with respect to the imaging system including the X-ray tube 11 and the X-ray detector 12, on the basis of the tabletop position information attached to the past image.

Therefore, the positional relationship calculating function 53 can perform positioning for the main scan using only the criterial image 71 imaged before the main scan. Hence, compared with the case where the positioning for the main scan is performed using the scanogram of the whole body, the exposure dose of the object in the scanography can be reduced because only a part of object P needs to be imaged by the scanography (see FIG. 3).

Next, the scanography for setting the tube current value in the main scan with the tube current modulation will be described.

Conventionally, when the main scan with tube current modulation is performed, scanography for setting the tube current value is usually performed before the main scan. The scanography is performed through the range including the scan range of the main scan. For example, when the scan range of the main scan is from the neck to the pelvis, conventionally, scanogram data from the neck to the pelvis is acquired before the main scan, and the change pattern of the tube current for controlling the tube current during the main scan is determined on the basis of this scanogram data.

In order to set the tube current value, it is sufficient to obtain scanogram data of each discrete position (hereinafter referred to as scan point) of a plurality of discrete positions along the body axis direction of the object P within the scan range of the main scan. However, object P is subjected to unnecessary exposure in the conventional method by the scanography other than the scan points.

Figure 5A:
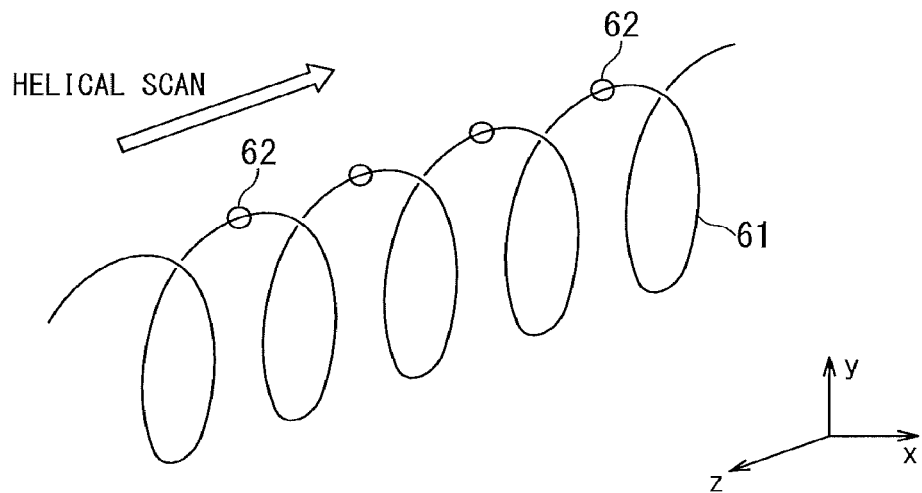
FIG. 5A is an explanatory diagram showing an example of scan points.
Figure 5B:
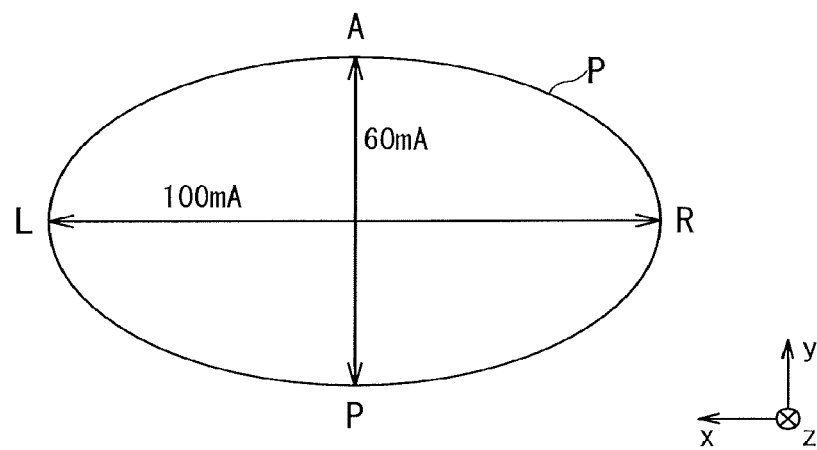
FIG. 5B is an explanatory diagram showing an example of how the tube current value is calculated from the scan data of the scan points.

FIG. 5A is an explanatory diagram showing an example of the scan points. FIG. 5B is an explanatory diagram showing an example of how the tube current value is calculated from the scan data of the scan points.

When the main scan is a helical scan, the scan point 62 is preferably set at a point that projects the AP direction (vertical direction, see FIG. 5A) or RL direction (horizontal direction) of the object P in the trajectory 61 of the X-ray tube 11 in the helical scan.

If there is scanogram data in the AP direction (or RL direction), since the area in terms of the elliptical water phantom and the length of the minor axis in the water equivalent thickness (or the length of the major axis) are determined, the length of the major axis (or the length of the minor axis) can be calculated. Therefore, the water equivalent thickness converted into the elliptical water phantom at each scan point 62 is obtained only by the scanogram data in the AP direction (or RL direction). Hence, the tube current value to be set at each scan point 62 can be obtained from the scanogram data of each scan point 62 (see FIG. 5B).

In this way, by performing the pulse scanography to acquire discrete images only at the plurality of discrete positions (scan points 62) along the body axis direction of object P, it is possible to set at least one of the tube current value and the tube voltage values corresponding to the scan range of the main scan as one of the scan conditions of the main scan, and is possible to greatly reduce the exposure dose of the object P compared with the case of performing the scanography from the neck to the pelvis before the main scan.

The processing circuitry 45 according to the present embodiment therefore performs the pulse scanography only at the scan points 62 (the plurality of discrete positions along the body axis direction of the object P) as the scanography, performed before the main scan, for setting at least one of the tube current values and the tube voltage values corresponding to the scan range of the main scan as one of the imaging conditions.

In order to more accurately obtain each position of the scan points 62, the positional relationship calculating function 53 firstly calculates the positional relationship between each position of the scan points 62 and the scan range of the main scan on the basis of the reference image and the criterial image 71 imaged before the main scan. More specifically, the positional relationship calculating function 53 performs positioning (setting of the scan range) for the main scan on the basis of the reference image and the criterial image 71 imaged before the main scan, and then calculates the positional relationship between each position of the scan points 62 and the scan range of the main scan, on the basis of the information on the set scan range, the rotation speed of the imaging system included in the imaging conditions of the main scan with tube current modulation or tube voltage modulation, and the relative speed between the tabletop 33 and the imaging system. To perform positioning for the main scan before the pulse scanography allows the positional relationship calculating function 53 to easily and accurately determine the positions of the scan points within the scan range of the main scan as compared to the case without positioning for the main scan.

Figure 6:
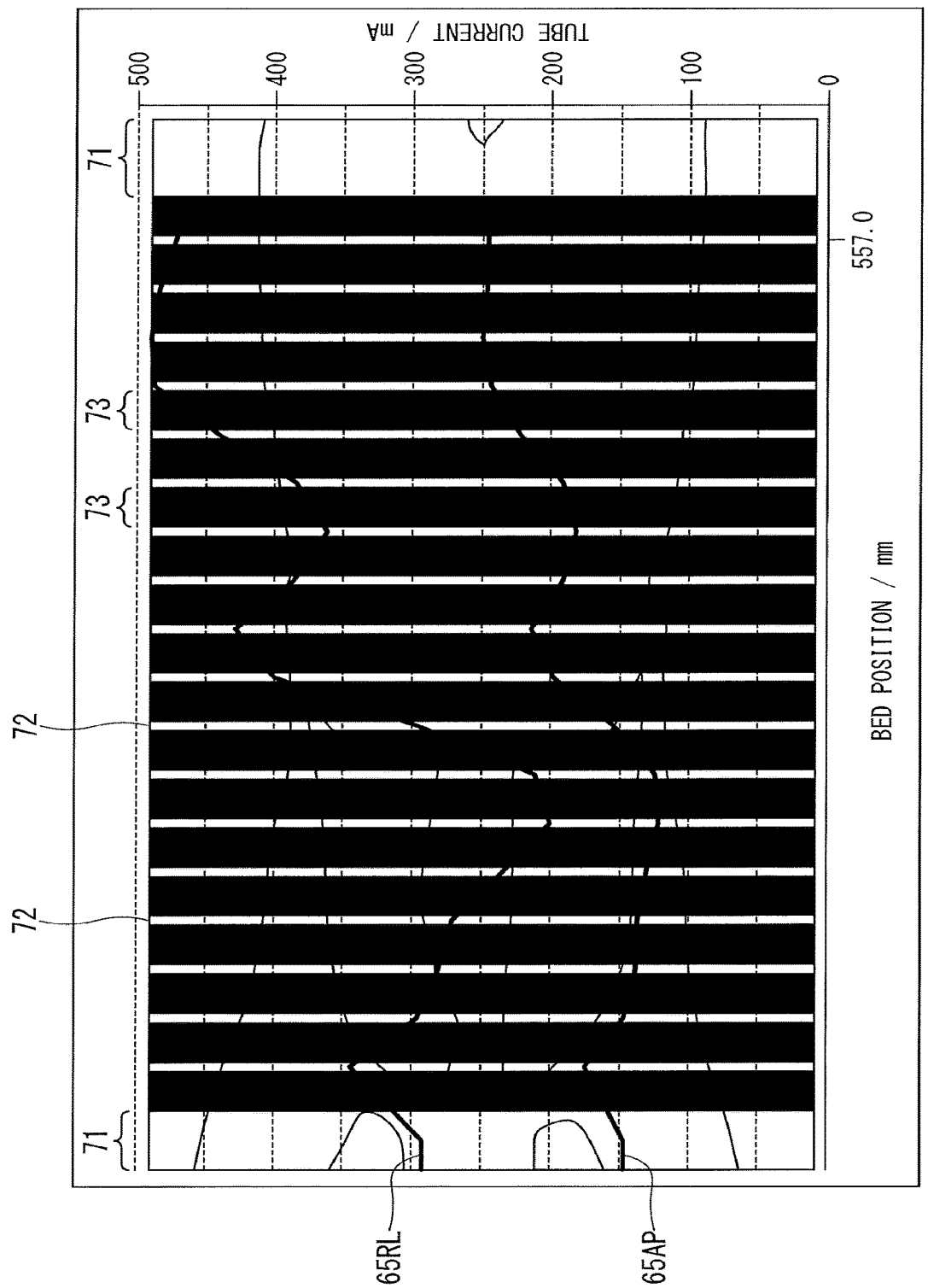
FIG. 6 is an explanatory diagram showing an example of the discrete images acquired only at positions corresponding to the scan points.

FIG. 6 is an explanatory diagram showing an example of the discrete images acquired only at positions corresponding to the scan points.

The imaging function 52 acquires the plurality of the discrete images (hereinafter referred to as a pulse scanogram) by performing the pulse scanography (intermittent scanography) of the object P only at the corresponding plurality of discrete positions 72 each corresponding to the scan point 62, the discrete positions 72 being calculated by the positional relationship calculating function 53 in order to set the tube current value in the main scan with tube current modulation, or to set the tube voltage value in the main scan with tube voltage modulation. At this time, scanography is not performed at the non-radiation position 73 except the position 72 corresponding to the scan point 62. That is, the plurality of discrete images is acquired by repeating ON and OFF of the X-ray irradiation at the plurality of discrete positions (the scan points 62) in the body axis direction of the object P.

Hence, in scanography for setting at least one of the tube current values and the tube voltage values corresponding to the scan range, the exposure dose of the object P can be greatly reduced as compared with the case of performing scanography in the entire scan range of the main scan.

For example, a case is assumed where the main scan is a helical scan in which the tabletop 33 and the imaging system are changing their positional relationship at a predetermined constant relative speed and in which the imaging system is rotating during imaging, and it is assumed that the rotating speed of the imaging system is 0.5 seconds/rotation. In this case, the imaging function 52 acquires the imaging condition of the main scan including the information such as the rotation speed from the memory 41 or the cloud server or the like via the network. The imaging function 52 is then able to image the pulse scanogram comprising only the position 72 corresponding to the scan point 62, by intermittently imaging the scanogram every 0.5 seconds with changing the relative position of the tabletop 33 and the imaging system at the same speed as the main scan.

The discrete image acquisition function 54 obtains the pulse scanogram (imaged at the plurality of discrete positions in the body axis direction of the object P) imaged by the gantry device 10 under the control of the imaging function 52 or imaged by an external imaging device.

The positional relationship calculating function 53 may improve the accuracy of the scan range by adjusting the scan range using the pulse scanogram. In this case, since it is possible to perform positioning for the main scan using only the criterial image 71 and the pulse scanogram imaged before the main scan, the exposure dose of the object P can be greatly reduced by the existence of the non-radiation positions 73 compared with the case where the positioning for the main scan is performed using the scanogram of the whole body.

Further, in the example explained above, the scanography along one direction such as the AP direction (or the RL direction) is replaced by the pulse scanography, but the scanography can be performed along two directions such as both in the AP direction and the RL direction. In this case, by replacing with the pulse scanography in at least one direction, it is possible to greatly reduce the exposure dose of the object P compared with the case where scanography is performed through entire scan ranges in both directions.

The positional relationship calculating function 53 may display on the display 42 the past image of the object P obtained by the modality or the optical camera in advance, and determine the position 72 to be imaged by the pulse scanography on the basis of the position instructed by the user via the input interface 43 while recognizing the displayed past image.

The pulse scanography for setting the tube current value is preferably executed for every main scan, even if the tube current value has already set for the same object P recently such as the previous day. This is because there is a possibility that the absorbed dose may change depending on the state of object P.

Further, as described above, the imaging of the criterial image 71 and the pulse scanography for setting the tube current value may be included in the same scan protocol.

Figure 7:
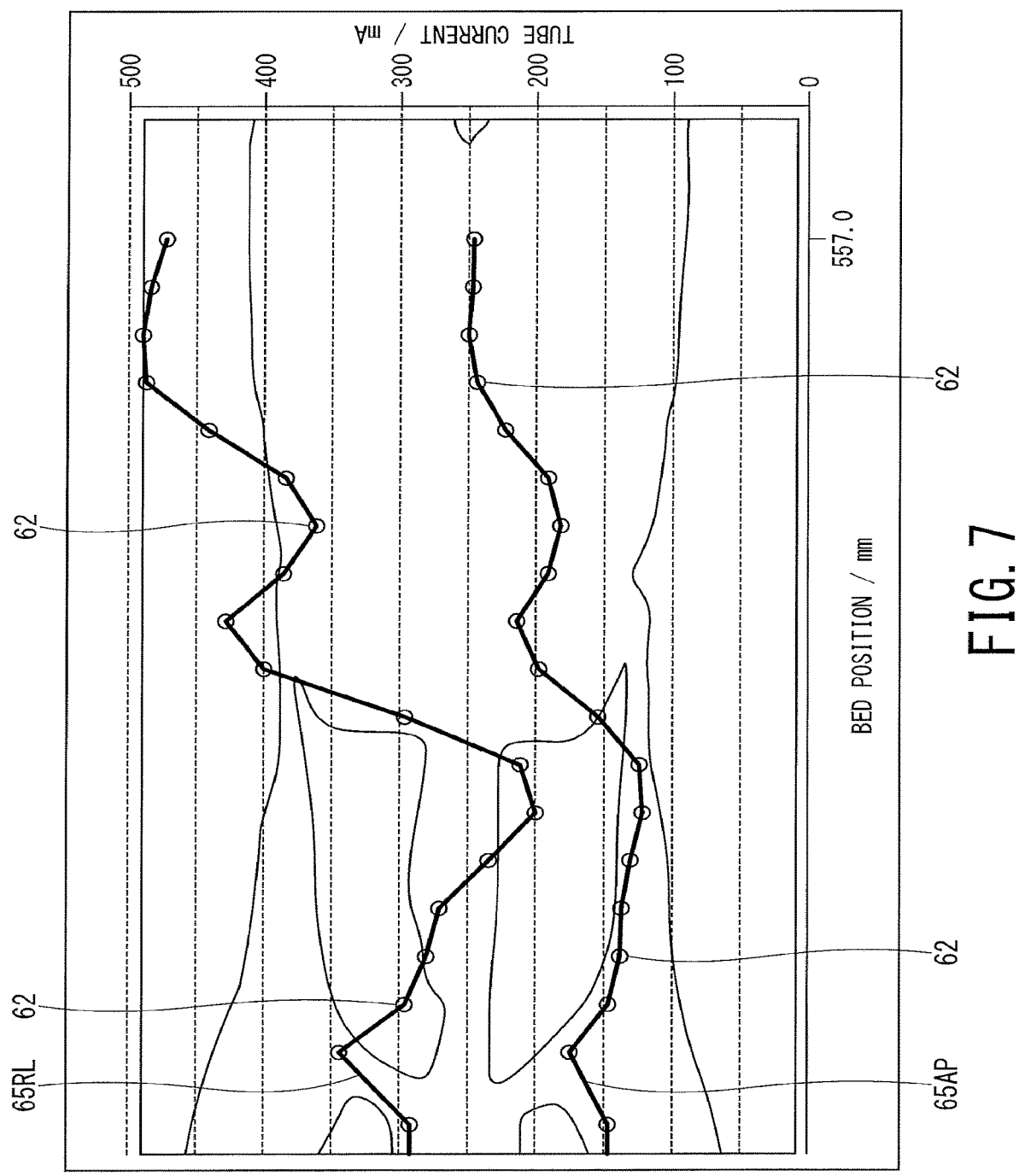
FIG. 7 is an explanatory diagram showing an example of a tube current value in the AP direction and a tube current value in the RL direction set for each scan point.

FIG. 7 is an explanatory diagram showing an example of a tube current value in the AP direction and a tube current value in the RL direction set for each scan point.

The imaging condition calculating function 55 calculates the imaging conditions corresponding to the scan range of the main scan based on the pulse scanogram for each position 72 corresponding to the scan point 62. For example, when the main scan is tube current modulation imaging, the imaging condition calculating function 55 calculates the tube current value for each scan point 62, and based on the tube current value for each scan point 62, calculates the tube current values corresponding to the scan range of the main scan (See FIG. 7).

Next, an example of the operation of the X-ray CT apparatus 1 according to the present embodiment will be described. In the following description, an example in the case of performing the main scan with tube current modulation is shown.

Figure 8:
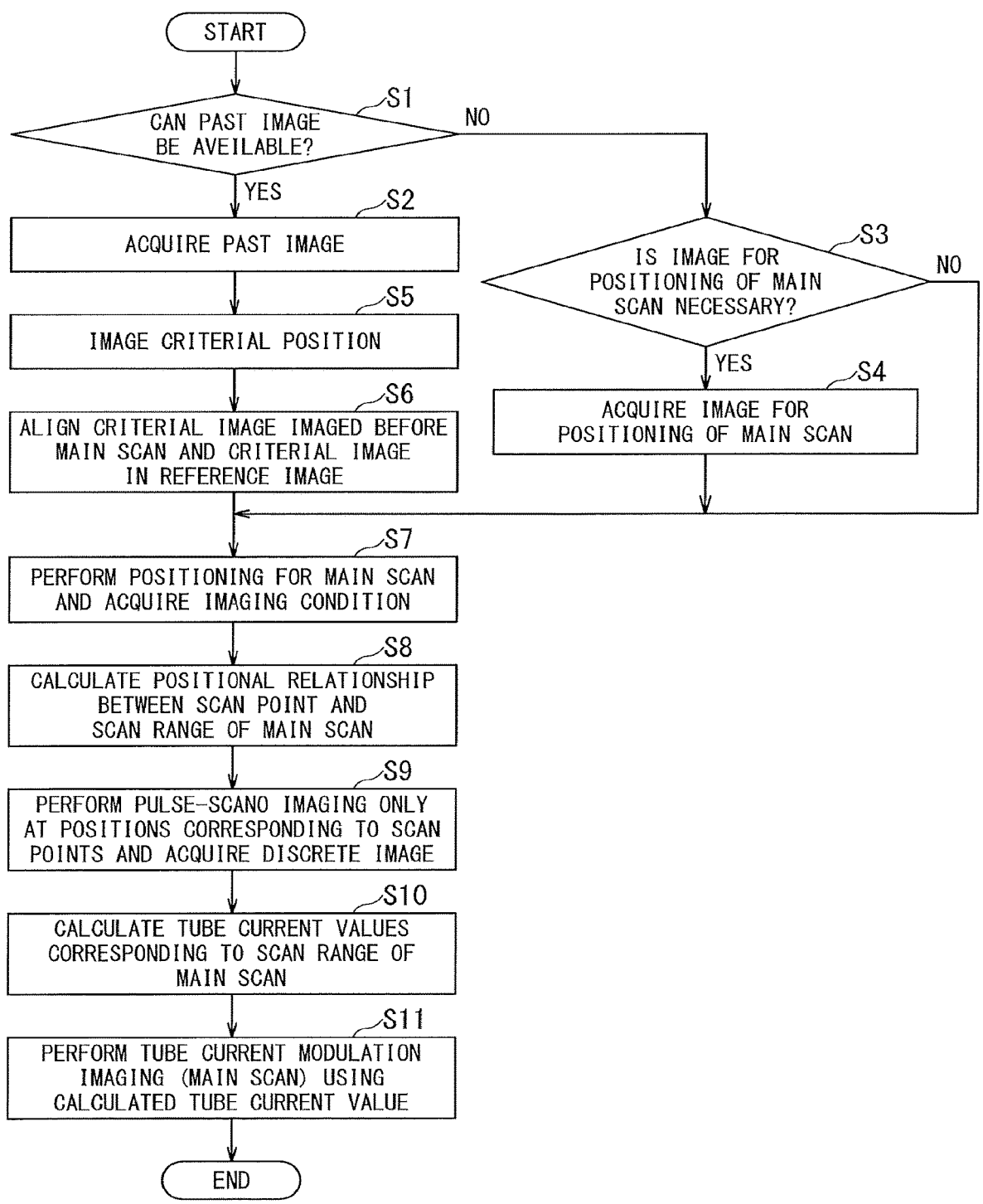
FIG. 8 is a flowchart showing an example of a procedure for reducing the exposure dose of the object in scanography performed before the main scan for positioning for the main scan and for setting of imaging conditions for the main scan, by the processor of the processing circuitry.

FIG. 8 is a flowchart showing an example of a procedure for reducing the exposure dose of the object P in scanography performed before the main scan for positioning for the main scan and for setting of imaging conditions for the main scan, by the processor of the processing circuitry 45. In FIG. 8, a reference character with "S" followed by a number such as "S1" denotes each step of the flowchart.

This procedure is started when information on the past image including the predetermined criterial position of the object P is acquired from the memory 41 or from the image server or the like via the network.

First in step S1, the criterial position image acquisition function 51 determines whether or not the past image can be available as the positioning image for the main scan (the image used in the positioning for the main scan).

Figure 9:
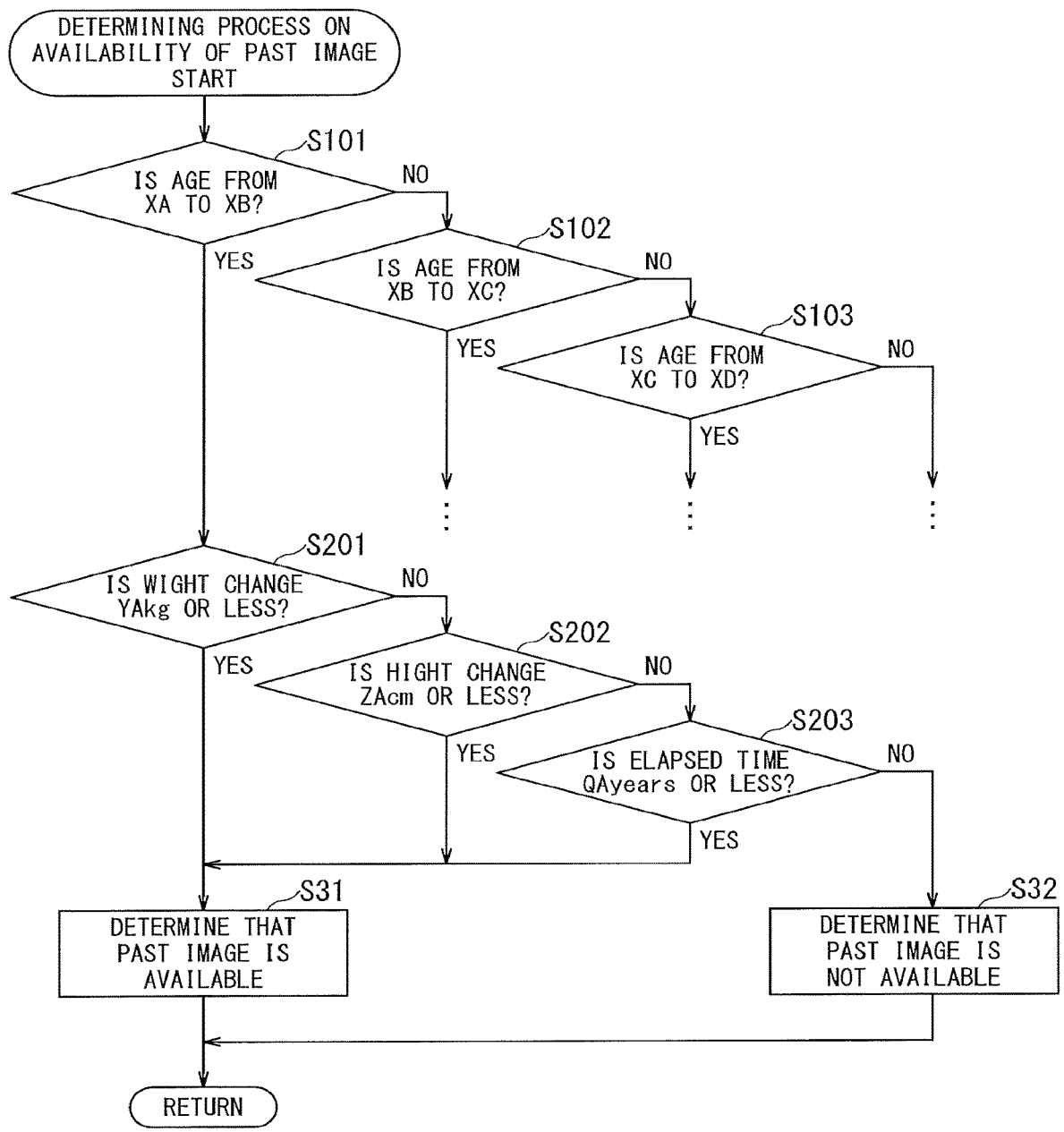
FIG. 9 is a flowchart showing an example of a procedure of a determining process on availability of the past image, executed by the criterial position image acquiring function in step S1 of FIG. 8.

FIG. 9 is a flowchart showing an example of a procedure of the determining process on availability of the past image, executed by the criterial position image acquiring function 51 in step S1 of FIG. 8.

The criterial position image acquisition function 51 determines availability of using the past image as the positioning image for the main scan on the basis of the change of the shape of the object P between the shape at the present time and the shape at the time when the past image was imaged. For example, the criterial position image acquisition function 51 firstly determines the age range to which the object P belongs (steps S101 to S103).

Next, when the threshold values expected significant change in the shape of object P, such as the threshold value of weight change set for each age range (step S201), a threshold value of height change (step S202), an elapsed time period from the imaging time of the past image to the present time (Step S203), and the like, is not exceeded, the criterial position image acquisition function 51 determines that the past image can be used for positioning for the main scan (step S31), and the process proceeds to step S2 of FIG. 8. Meanwhile, when the threshold values expected significant change in the shape of object P is exceeded, the criterial position image acquisition function 51 determines that the past image should not be used for positioning for the main scan (step S32), and the process proceeds to step S3 in FIG. 8.

When it is determined in step S31 of FIG. 9 that the past image can be used for positioning for main scan, proceeding to step S2 of FIG. 8, and the criterial position image acquisition function 51 acquires the past image including the predetermined criterial position of the object P from the memory 41 or from the image server or the like via the network.

When it is determined in step S32 of FIG. 9 that the past image should not be used for positioning for the main scan, proceeding to step S3 of FIG. 8, and the criterial position image acquisition function 51 determines whether or not the positioning image is necessary. When the positioning image for main scan is necessary, the process proceeds to step S4.

Meanwhile, when the positioning image for main scan is unnecessary, the process proceeds to step S7. For example, when the tube current modulation imaging is performed without strict positioning using the scanogram, as is often the case in the health checks, a positioning image for the main scan is unnecessary.

In the present embodiment, the example in which the step S3 for determining necessity of the positioning image for the main scan is executed after the step S1 is shown, but the step S3 may be executed before the step S1. In this case, when it is determined that the positioning image for the main scan is necessary, the process of step S1 is executed, and when it is determined to be unnecessary, the process proceeds to step S7. In this case, the positioning for the main scan by the positional relationship calculating function 53 will be omitted regardless of whether or not the past image is available.

In step S3, when it is determined that the positioning image for main scan is necessary, in step S4 the criterial position image acquisition function 51 acquires the reference image for positioning for the main scan including the predetermined criterial position of the current object P, and the process proceed to step S7. The newly acquired reference image for positioning for the main scan may be the image obtained by the optical camera in step S4 or the scanogram imaged again in step S4 by the X-ray CT apparatus 1. Note that when imaging a scanogram again, the imaging range of the scanography is adequate as long as the scan range of the main scan can be set from the scanogram. The scanogram in this case may be imaged during the execution of the same protocol as the pulse scanography executed in step S9, for example.

Next, in step S5, the imaging function 52 images the criterial image 71 including the predetermined criterial position of the object P before the main scan (see FIGS. 3 and 4A). This imaging may be performed during the execution of the same protocol as the pulse scanography executed in step S9.

Next, in step S6, the positional relationship calculating function 53 aligns the criterial image 171 of the reference image and the criterial image 71 imaged before the main scan (see FIG. 4B).

Next, in step S7, the positional relationship calculating function 53 performs positioning for the main scan to set the scan range, and acquires the imaging conditions for the main scan with tube current modulation from the memory 41 or from the cloud server or the like via the network.

Next, in step S8, the positional relationship calculating function 53 calculates the positional relationship between each position of the scan points 62 and the scan range of the main scan on the basis of the reference image, the criterial image 71 imaged before the main scan, and the imaging conditions of the main scan (See FIG. 5A). When there is no reference image or criterial image 71, the positional relationship may be obtained based on the imaging conditions of main scan.

Next, in step S9, the imaging function 52 performs the pulse scanography of the object P only at the position 72 corresponding to the scan point 62 determined by the positional relationship calculating function 53. The discrete image acquisition function 54 acquires the plurality of discrete images (pulse scanogram) obtained by the pulse scanography (see FIG. 6).

Next, in step S10, the imaging condition calculation function 55 calculates the tube current values corresponding to the scan range of the main scan on the basis of the pulse scanogram of each position 72 corresponding to the scan point 62 (see FIG. 7).

Next, in step S11, the imaging function 52 performs the main scan with tube current modulation on the basis of the tube current values of the scan range of the main scan calculated by the imaging condition calculating function 55, and the series of the procedures is completed.

Any one of the aforementioned embodiments can reduce the exposure dose of the object in scanography, which is performed before the main scan, for positioning for the main scan and for the setting of the imaging conditions for the main scan.

The processing circuitry 45 in the present embodiment is an example of the processing circuitry recited in the claims.

Further, the processing circuitry in the above-described embodiments is an example of the processing circuitry described in the claims. In addition, the term "processor" used in the explanation in the above-described embodiments, for instance, refer to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising image processing circuitry configured to:
   acquire a plurality of discrete images at a corresponding plurality of non-continuous discrete positions in a body axis direction of an object; and
   calculate imaging conditions corresponding to a scan range of a main scan, based on the plurality of discrete images.

2. The X-ray CT apparatus of claim 1, wherein the image processing circuitry acquires the plurality of discrete images by repeating ON and OFF of an X-ray irradiation at the plurality of non-continuous discrete positions in the body axis direction of the object.

3. The X-ray CT apparatus of claim 1, wherein the image processing circuitry calculates as the imaging conditions at least one of tube current values and tube voltage values corresponding to the scan range of the main scan.

4. The X-ray CT apparatus of claim 3, wherein the image processing circuitry calculates the tube current value at each of the plurality of non-continuous discrete positions based on each of the plurality of discrete images corresponding to each of the plurality of non-continuous discrete positions, and calculates the tube current values corresponding to the scan range of the main scan based on the calculated tube current value at the each of the plurality of non-continuous discrete positions.

5. The X-ray CT apparatus of claim 4, wherein the image processing circuitry performs the main scan with tube current modulation using the calculated tube current values corresponding to the scan range of the main scan.

6. The X-ray CT apparatus of claim 1, wherein the image processing circuitry
   acquires a reference image that includes a criterial position in the object and a criterial image that includes the criterial position and is imaged during execution of a scan protocol in which the plurality of discrete images is acquired, and
   calculates a positional relationship between the plurality of non-continuous discrete positions and the scan range of the main scan based on the reference image and the criterial image.

7. The X-ray CT apparatus of claim 6, wherein the image processing circuitry calculates each of the plurality of non-continuous discrete positions positioned within the scan range of the main scan, based on a rotational speed of an imaging system in the main scan and a relative speed between a tabletop on which the object is placed and the imaging system.

8. The X-ray CT apparatus of claim 6, wherein the image processing circuitry acquires, as the reference image, a past image including the criterial position acquired by imaging the object in a past with a modality or an optical camera.

9. The X-ray CT apparatus of claim 6, wherein the image processing circuitry acquires, as the reference image, a scanogram including the criterial position acquired by performing the scanography of the object in a past.

10. The X-ray CT apparatus of claim 8, wherein the image processing circuitry determining availability of using the past image as the reference image based on a change of a shape of the object between a shape at a present time and a shape at a time when the past image was imaged.

11. The X-ray CT apparatus of claim 10, wherein the image processing circuitry acquires the past image as the reference image when the image processing circuitry determines it is available to use the past image as the reference image, while the image processing circuitry acquires an image of the object of the present as the reference image when the image processing circuitry determines it is unavailable to use the past image as the reference image.

12. The X-ray CT apparatus of claim 6, wherein the processing circuit aligns the reference image and the criterial image by adjusting a relative position between a tabletop and an imaging system based on the criterial image and a positional information of the tabletop attached to the reference image.

13. An imaging method comprising:
    acquiring a plurality of discrete images at a corresponding plurality of non-continuous discrete positions in a body axis direction of an object to be imaged using a medical imaging apparatus;
    calculating imaging conditions corresponding to a scan range of a main scan to be performed using the medical imaging apparatus, based on the plurality of discrete images; and
    controlling the medical imaging apparatus to perform the main scan using the calculated imaging conditions.

14. The X-ray CT apparatus as claimed in claim 1, wherein the image processing circuitry is further configured to control the X-ray CT apparatus to perform the main scan using the calculated imaging conditions.

15. The imaging method as claimed in claim 13, wherein the medical imaging apparatus comprises an X-ray CT apparatus.

16. The imaging method as claimed in claim 13, wherein the acquiring the plurality of discrete images comprises acquiring the plurality of discrete images by repeating ON and OFF of an X-ray irradiation at the plurality of non-continuous discrete positions in the body axis direction of the object.

17. The imaging method as claimed in claim 13, wherein the calculating the imaging conditions comprises calculating at least one of tube current values and tube voltage values corresponding to the scan range of the main scan.

* * * * *